(12) United States Patent
Whittemore

(10) Patent No.: US 11,833,266 B2
(45) Date of Patent: Dec. 5, 2023

(54) CARD DISTRIBUTION AND SANITIZING APPARATUS USING ULTRAVIOLET IRRADIATION

(71) Applicant: Wynn Resorts Holdings, LLC, Las Vegas, NV (US)

(72) Inventor: Ellen F. Whittemore, Las Vegas, NV (US)

(73) Assignee: Wynn Resorts Holdings, LLC, Las Vegas, NV (US)

( * ) Notice: Subject to any disclaimer, the term of this patent is extended or adjusted under 35 U.S.C. 154(b) by 493 days.

(21) Appl. No.: 17/157,773

(22) Filed: Jan. 25, 2021

(65) Prior Publication Data

US 2022/0233735 A1 Jul. 28, 2022

(51) Int. Cl.
*A61L 2/24* (2006.01)
*A61L 2/10* (2006.01)
*A63F 1/14* (2006.01)

(52) U.S. Cl.
CPC .......... *A61L 2/24* (2013.01); *A61L 2/10* (2013.01); *A63F 1/14* (2013.01); *A61L 2202/11* (2013.01); *A61L 2202/14* (2013.01)

(58) Field of Classification Search
CPC .......... A61L 2/24; A61L 2/10; A61L 2202/11; A61L 2202/14; A61L 2202/122; A61L 2202/16; A63F 1/14; A63F 2250/54
See application file for complete search history.

(56) References Cited

U.S. PATENT DOCUMENTS

| | | | | |
|---|---|---|---|---|
| 5,428,856 A | * | 7/1995 | Thorne | B08B 1/02 134/9 |
| 6,311,974 B1 | * | 11/2001 | Koga | G07F 17/3202 463/20 |
| 7,038,219 B2 | | 5/2006 | Clark et al. | |
| 7,397,041 B1 | * | 7/2008 | Leonard | A61L 2/10 250/455.11 |
| 7,658,891 B1 | * | 2/2010 | Barnes | C01B 13/11 128/205.28 |

(Continued)

FOREIGN PATENT DOCUMENTS

| | | |
|---|---|---|
| CN | 108298194 | 7/2018 |
| KR | 20130000082 | 1/2013 |

(Continued)

OTHER PUBLICATIONS

Zender, Bill, Developing a coronavirus protection strategy for casinos and cardrooms, Casino Journal, Apr. 23, 2020, 9 pages.

*Primary Examiner* — David A Vanore
(74) *Attorney, Agent, or Firm* — Brownstein Hyatt Farber Schreck, LLP

(57) ABSTRACT

A card distribution and sanitization apparatus, such as a dealing shoe, may use ultraviolet light to sanitize the surface of playing cards. The ultraviolet light may be directed to an outlet and/or interior cavity of the card distribution and sanitization apparatus and may be configured to emit light in the 200 nm to 290 nm wavelength range. An enclosure of the card distribution and sanitization apparatus may be coupled to ultraviolet light-emitters and may be configured to hold the playing cards and the ultraviolet light-emitters. An associated controller may control operations of the card distribution and sanitization apparatus.

20 Claims, 10 Drawing Sheets

(56) References Cited

U.S. PATENT DOCUMENTS

| | | | | |
|---|---|---|---|---|
| 8,308,163 | B2* | 11/2012 | Shigeta | A63F 1/14 |
| | | | | 273/149 R |
| 9,999,699 | B2 | 6/2018 | Sinai | |
| 10,366,576 | B2* | 7/2019 | Shigeta | A63F 1/14 |
| 11,040,271 | B1* | 6/2021 | Sines | A61L 2/10 |
| 2009/0252646 | A1 | 10/2009 | Holden et al. | |
| 2021/0369889 | A1* | 12/2021 | Fekete | A63F 1/06 |
| 2021/0379221 | A1* | 12/2021 | Ridell | A61L 2/10 |
| 2022/0233735 | A1* | 7/2022 | Whittemore | A61L 2/24 |

FOREIGN PATENT DOCUMENTS

| | | |
|---|---|---|
| KR | 20140005693 | 1/2014 |
| WO | WO2013/068973 | 5/2013 |

* cited by examiner

CARD DISTRIBUTION AND SANITIZING APPARATUS USING ULTRAVIOLET IRRADIATION

FIELD

Embodiments described herein generally relate to a card distribution apparatus and, in particular, to systems, methods, and components for sanitizing cards using ultraviolet light irradiation.

BACKGROUND

Cards are ordinarily provided to players for use in a card game, such as poker, bridge, or blackjack. Dealing shoes, otherwise known as card shoes, may be used to hold one or multiple decks, or sets, of cards and individual, or sets of, cards may be distributed to players during the course of a card game. After distribution, cards are typically picked up or otherwise touched by players. Once the card game, or a portion of the card game, is completed, used cards may be returned to a dealer who may shuffle and return the used cards to the dealing shoe or directly to the players. The same cards, therefore, may be distributed many times to many different players over the course of one or multiple card games.

As with any physical item that may be in contact with multiple people, contaminants may be present on the surface of the cards. Accordingly, there may be a risk that contaminants may be transferred between players and dealers. The systems and techniques described herein may be used to reduce the presence of various contaminants by using ultraviolet irradiation.

SUMMARY

In some embodiments described herein, a card distribution and sanitization apparatus for disinfecting a set of cards may be provided. The apparatus may comprise a power supply and an enclosure. The enclosure may define an interior cavity configured to support the set of cards and may comprise a front wall defining a gap configured to allow a card of the set of cards to be removed from the interior cavity. A card sanitizing stack-up coupled to the enclosure may additionally be provided. The card sanitizing stack-up may define an outlet configured to receive the card of the set of cards after the card passes through the gap. The card sanitizing stack-up may comprise a first light-emitter operably coupled to the power supply and configured to emit light toward a first side of the card as the card moves through the outlet, a first optical diffuser coupled to the first light-emitter and configured to distribute light emitted from the first light-emitter to the first side of the card, a second light-emitter separated from the first light-emitter by at least the outlet and operably coupled to the power supply. The second light-emitter may be configured to emit light toward a second side of the card as the card moves through the outlet, the second side of the card opposite from the first side of the card. The card sanitizing stack-up may additionally comprise a second optical diffuser coupled to the second light-emitter and configured to distribute light emitted from the second light-emitter to the second side of the card. The card distribution and sanitization apparatus may additionally comprise a controller operably coupled to the power supply and configured to control the first light-emitter and the second light-emitter to disinfect both the first side and the second side of the card as the card passes through the outlet.

The enclosure may comprise a base plate, a first side wall extending from a first end of the base plate, and a second side wall extending from a second end of the base plate, the first end opposite from the second end. The front wall may be coupled to the first side wall and the second side wall. The base plate, the first side wall, the second side wall, and the front wall may define the interior cavity. The base plate may be coupled to the card sanitizing stack-up outside of the interior cavity.

Light emitted by both the first light-emitter and the second light-emitter may have a wavelength between 200 nm and 290 nm. The controller may be configured to operate the first light-emitter and the second light-emitter at a duration to cause at least a portion of microorganisms present on a surface of the card to be ruptured.

At least one of the first optical diffuser or the second optical diffuser may physically guide the card as the card passes through the outlet, such that the card is in contact with the at least one of the first optical diffuser or the second optical diffuser. A proximity sensor configured to detect a presence of the card at the outlet may additionally be provided.

The controller may direct at least one of the first light-emitter or the second light-emitter to begin emitting light after the proximity sensor detects the presence of the card at the outlet. The controller may increase an intensity of at least one of the first light-emitter or the second light-emitter after the proximity sensor detects the presence of the card at the outlet.

A card distribution and sanitization apparatus may comprise a housing defining an interior cavity configured to support a set of cards and an outlet for a card of the set of cards to pass through, the outlet positioned at a front portion of the housing. The card distribution and sanitization apparatus may additionally comprise a light-emitting stack-up positioned proximate to the outlet and defining an inlet for receiving the card. The light-emitting stack-up may comprise a first light-emitter configured to emit light toward the card as the card passes through the light-emitting stack-up and a second light-emitter configured to emit light toward the card as the card passes through the light-emitting stack-up. The first light-emitter and the second light-emitter may be separated by a passage of the light-emitting stack-up. The card distribution and sanitization apparatus may additionally comprise a controller operatively coupled to the first light-emitter and the second light-emitter and configured to operate the first light-emitter and the second light-emitter to administer a dosage of UV light toward the card causing at least a partial sanitization of a surface of the card.

At least one of the first light-emitter or the second light-emitter may be an elongated light-emitter. In some cases, the elongated light-emitter may be a light-emitting strip, the light-emitting strip comprising a number of light-emitting diode elements. In additional or alternate cases, the elongated light-emitter may be an ultraviolet light-emitting tube.

The card distribution and sanitization apparatus may further comprise a third light-emitter coupled to an internal wall of the housing. The third light-emitter may be configured to emit UV light onto the set of cards within the internal cavity.

The card distribution and sanitization apparatus may further comprise a friction strip coupled to the internal wall of the housing. The friction strip may be configured to separate successive cards of the set of cards.

The housing may further comprise a lid and the controller may cause the first light-emitter and the second-light emitter to stop emitting light when the lid is opened.

The light-emitter may administer a dosage of UV light of at least 40 mJ/cm². The card distribution and sanitization apparatus may comprise a proximity sensor and the controller may operate the first light-emitter and the second light-emitter to administer the dosage of UV light toward the card in response to the proximity sensor detecting the card.

A card distribution and sanitization apparatus may comprise a housing defining an interior cavity configured to support a set of cards and a gap for a card of the set of cards to pass through, the gap positioned at a front portion of the housing. The card distribution and sanitization apparatus may further comprise a light-emitting stack-up positioned proximate to the gap and configured to receive the card after the card passes through the gap. The light-emitting stack-up may define an inlet and a passage and the light-emitting stack-up may comprise a pair of light-emitters positioned on opposing sides of the passage and configured to emit ultraviolet light toward the card.

The pair of light-emitters may be configured to emit ultraviolet-C light toward a respective card of the set of cards as the respective card passes through the passage. The pair of light-emitters may be configured to administer a dosage of ultraviolet light of at least 40 mJ/cm².

The card distribution and sanitization apparatus may further comprise an optical detector configured to measure a dosage value of ultraviolet light emitted from the pair of light-emitters and a controller configured to determine whether the dosage value meets or surpasses a threshold value and direct the pair of light-emitters to stop emitting ultraviolet light when the dosage value meets or surpasses the threshold value.

BRIEF DESCRIPTION OF THE DRAWINGS

Reference will now be made to representative embodiments illustrated in the accompanying figures. It should be understood that the following descriptions are not intended to limit the embodiments to one preferred embodiment. To the contrary, they are intended to cover alternatives, modifications, and equivalents as may be included within the spirit and scope of the described embodiments as defined by the appended claims. Identical reference numerals have been used, where possible, to designate identical features that are common to the figures.

Figure 1:
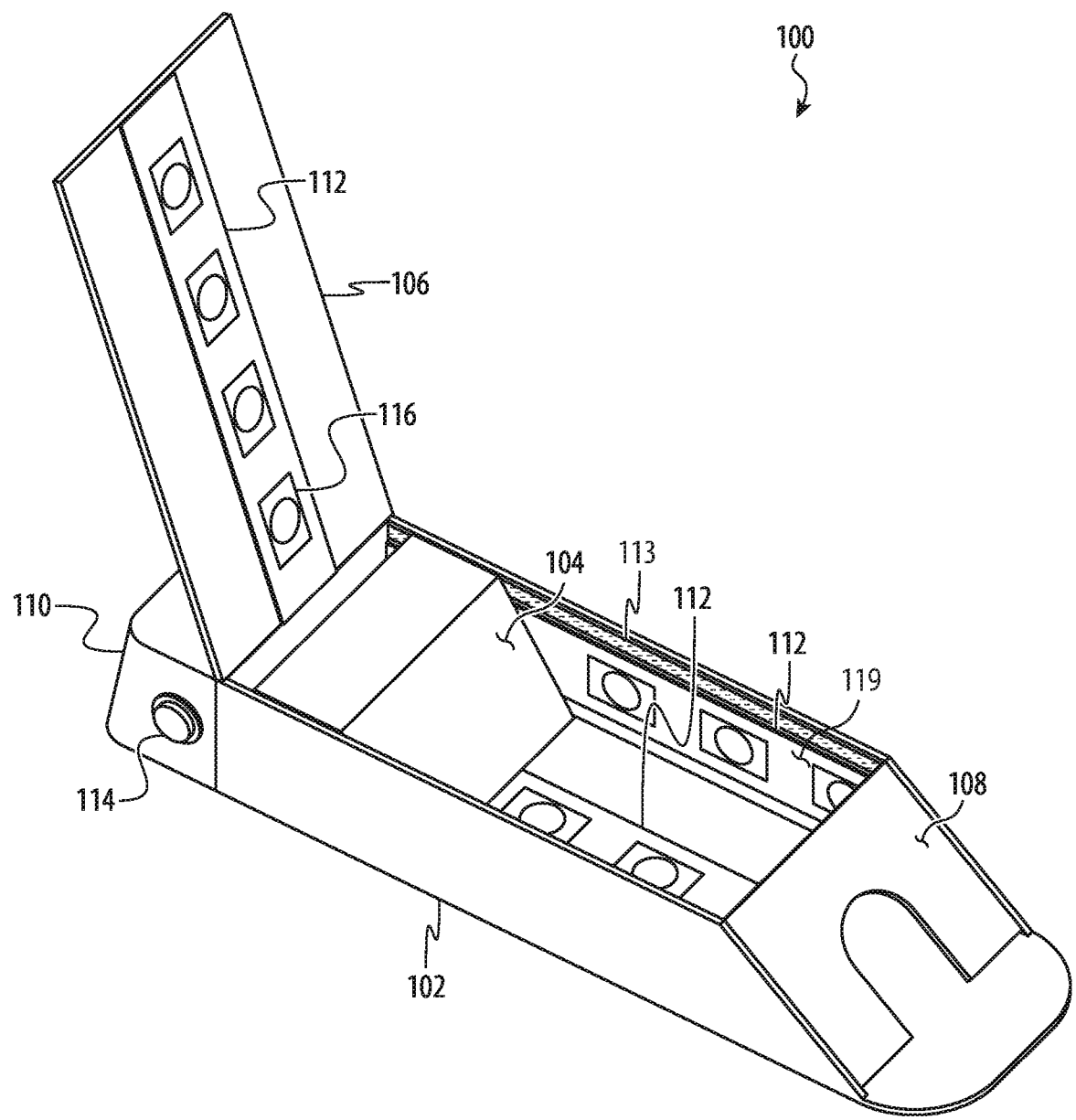
FIG. 1 depicts an example card distribution and sanitization apparatus including multiple light-emitting elements, as described herein.

The use of cross-hatching or shading in the accompanying figures is generally provided to clarify the boundaries between adjacent elements and also to facilitate legibility of the figures. Accordingly, neither the presence nor the absence of cross-hatching or shading conveys or indicates any preference or requirement for particular materials, material properties, element proportions, element dimensions, commonalities of similarly illustrated elements, or any other characteristic, attribute, or property for any element illustrated in the accompanying figures.

Additionally, it should be understood that the proportions and dimensions (either relative or absolute) of the various features and elements (and collections and groupings thereof) and the boundaries, separations, and positional relationships presented therebetween, are provided in the accompanying figures merely to facilitate an understanding of the various embodiments described herein and, accordingly, may not necessarily be presented or illustrated to scale, and are not intended to indicate any preference or requirement for an illustrated embodiment to the exclusion of embodiments described with reference thereto.

DETAILED DESCRIPTION

The embodiments described herein are generally directed to card distribution apparatuses and systems and methods for sanitizing cards held within card distribution apparatuses. Such card distribution apparatuses may use one or a number of ultraviolet light-emitters to emit ultraviolet light toward one card or a set of cards during a sanitization process (also referred to herein as "ultraviolet irradiation"). In a non-limiting example, a card distribution apparatus may include a base, a front wall, and a number of side walls connected to the base plate to define an interior cavity. Cards may be placed within the interior cavity and may be distributed or dealt to a player through a gap between the front wall and the base. Ultraviolet ("UV") light may be emitted within the interior cavity and/or near the gap to sanitize cards as they are held in the interior cavity and/or are distributed.

In some embodiments, a card distribution apparatus may be coupled to a power supply and may include one or a number of light-emitters operatively coupled to the power supply. The light-emitters may emit ultraviolet light (e.g., UV-C/Far-UV light) with a wavelength between 200 nm and 290 nm toward, near, or within portions of a card distribution apparatus.

Ultraviolet light, particularly UV-C light, may inactivate the reproduction of organic material by being absorbed by and denaturing proteins in DNA or RNA (e.g., thymine bases in DNA or RNA). In some instances, UV-C light may lead to a rupture of cellular walls and may directly kill, or otherwise destroy, microorganisms such as bacteria or viruses (e.g., SARS-CoV-2, MERS-CoV, *Escherichia coli*, and so on). In particular, microorganisms may be present on the surface of one or a number of cards within a deck of cards after being touched by players who are carriers of the particular microorganisms.

To properly destroy, deactivate, or otherwise harm the reproduction of microorganisms, a proper UV-C dosage may be required. As used herein, a dosage may additionally be referenced as an irradiation level. As used herein, dosage is calculated as: Dose=Intensity (I)×Exposure Time(t). Different microorganisms may typically require different dosages for sufficient destruction or deactivation, but a sufficiently high dose may destroy or deactivate a vast majority of harmful microorganisms. This sufficiently high dose may be reference herein as a "threshold dosage." Likewise, a "threshold time" may refer to a period of time that results in a threshold dosage given a constant intensity and a "threshold intensity" may refer to an intensity value that results in a threshold dosage given a constant exposure time. In some embodiments a threshold dosage may be from about 10 $mJ/cm^2$ to about 500 $mJ/cm^2$. In some embodiments, a threshold dosage may be about 40 $mJ/cm^2$, though other values may additionally be used. As used herein, the term "about" may be used to refer to a difference of +/−10% with respect to the given value.

In some embodiments, an intensity value of UV-C light may be limited by, for example, longevity or power concerns for the associated apparatus particularly when powered by one or multiple batteries. Systems of the present disclosure may account for light intensity limitations by increasing an exposure time and/or by initiating successive bursts of UV-C light over a time period.

In some embodiments, a card distribution apparatus may include a number of ultraviolet diode strips coupled along interior surfaces of a card distribution apparatus. In a non-limiting example, an ultraviolet diode strip may be affixed to each internal surface including an internal side of a top cover, an internal side of a first side wall, an internal side of a second side wall, and an internal side of a base. Each ultraviolet diode strip may be electrically connected in series, such that each ultraviolet diode is turned on or off synchronously with other ultraviolet diodes in the strip, or may be electrically connected in parallel so that each ultraviolet diode may be individually controlled and/or operated. In some embodiments, each ultraviolet diode strip may be positioned behind a light transmissive wall or a barrier layer in order to prevent direct contact with cards stored in a card distribution apparatus and/or to scatter light emitted from each ultraviolet diode strip.

In alternate or additional embodiments, a card distribution apparatus may include a card sanitizing stack-up coupled to a base plate and defining an outlet. An example card sanitizing stack-up may include first and second light-emitters and first and second optical diffusers to distribute emitted light. The first light-emitter and first optical diffuser may be separated from the second light-emitter and the second optical diffuser by a passage. A proximity sensor may be provided proximate to the outlet and may be configured to detect when a card is moving through the passage. Once a card is detected, the first and second light-emitters may be turned on and may stay on for a predetermined time period.

In some embodiments, an array or distribution of protrusions or other features may be disposed within internal surfaces of a card distribution apparatus (also referred to herein as "separation features"). The protrusions may be placed in order to separate successive cards from contacting each other so as to allow more UV-C light to reach otherwise hidden surfaces. Instead of, or in addition to, such protrusions, a friction strip may be provided to similarly separate successive cards of a set of cards. A card distribution apparatus may additionally include features such as automatic shut-off switches to minimize UV-C light from leaking into an external environment when a cover of the card distribution apparatus is opened and/or to shut-off when a certain level of heat is detected.

As used herein "cards" may refer to playing cards which may be marked with distinguishing symbols and may be made from paper, card stock, plastic, and so on. For example, cards may include colors (e.g., black and red), numbers, symbols (e.g., spades, hearts, clubs, and diamonds), a front face (e.g., a face depicting a number and symbol), and a back face (e.g., a uniform pattern identical to the back face of other cards in the deck). Such cards may additionally be referred to as "playing cards." A card may be part of a set or deck, referred to as, for example, a "deck of cards" or a "deck of playing cards," which may consist of, in a non-limiting example, 52 cards of varying symbols and numbers. The term "cards" may also refer to any piece of cardstock, plastic, paper, cardboard, and so on.

In accordance with the provided disclosure, a card distribution apparatus may be configured to hold one or a number of decks, or any subset thereof. In some embodiments, one deck of cards (e.g., about 52 cards) may be disposed in a card distribution apparatus. In some embodiments, multiple decks of cards may be disposed in a card distribution apparatus. In some cases, sets of cards may be less than 52 cards. The particular dimensions of any card distribution apparatus in accordance with the provided disclosure may be varied in accordance with desired capacity.

A light-emitter may refer to light-emitting diodes, elongated lamps, light-emitting tubes, incandescent bulbs, bulb-shaped light-emitters, any combination thereof, and so on. Any light-emitter, and associated structures including sleeves (e.g., quartz sleeves), mercury drops, insulating material, and so on, that may emit ultraviolet light having a wavelength between about 10 nm and about 400 nm may be used in accordance with the provided disclosure. More particularly, UV-C light having a wavelength of about 200 nm and about 290 nm may be used. As described above, the term "about" may refer to a value of +/−10% with respect to the given value.

The discussion herein with respect to card distribution and sanitization apparatuses relate more generally to ultraviolet and UV-C sanitization for cards. These and other embodiments are discussed with reference to FIGS. 1-9. However, those skilled in the art will readily appreciate that the detailed description given herein with respect to these figures is for explanatory purposes only and should not be construed as limiting.

FIG. 1 depicts a card distribution and sanitization apparatus 100 including a number of light-emitting strips 112 coupled to internal surfaces of the card distribution and sanitization apparatus 100. The card distribution and sanitization apparatus may further include an enclosure 102 defining a base and a number of side walls, a wedge 104, a lid 106, a front wall 108, a power supply 110, and a switch 114. The number of light-emitting strips 112 may comprise a number of resistors, light-emitters 116, and other electronic components, including electrically conductive traces and so on. In some embodiments, a friction strip 113 may be provided, as depicted in FIG. 1.

The enclosure 102 may include a lid 106. The lid 106 may be pivotally coupled to the enclosure 102 and may be opened or closed by a user. In some embodiments, the lid 106 may be operatively coupled to, for example, an electric motor and may open and close due to power obtained from the electric motor. In some embodiments, a light-emitting strip 112 and one or a number of light-emitters 116 may be coupled to the lid 106. In some embodiments, the enclosure 102 (including side walls and the base plate) and/or the lid 106 may include a number of protrusions or separations features that extend from the enclosure 102 and interact with a cards disposed within the enclosure 102. These separation features may prevent successive cards from coming into contact with each other and may allow the light-emitting strip 112 to direct ultraviolet light onto a front- or back-face of a cart. The separation features may be disposed along any surface and in any number and may separate all cards or some cards. The separation features may be formed of, for example, a plastic, a metal, a wood, and so on. The separation features may be forms as a bump or may be formed as any lengthened shape designed to separate stacked cards. In some cases, the friction strip 113 may act as a separation feature.

In some embodiments, the lid 106 may comprise a number of layers. For example, one layer may be an opaque layer made of metal or wood and another layer may be a light transmissive layer 119 made of glass or transparent plastic. In some embodiments, the light-emitting strip 112 may be positioned in between the layers. The light transmissive layer 119 may be formed as an inside layer and the opaque layer may be formed as an outside layer, so that light emitted from the light-emitting strip 112 may illuminate an interior cavity. In some embodiments, the light transmissive layer 119 may act as a diffusing layer and may diffuse light emitted from the light-emitting strip 112. In some embodiments, both the inside and the outside layer may be transparent (e.g., formed of a glass and/or a transparent plastic) so that a user may visually see the contents of the card distribution and sanitization apparatus 100 even while closed. The examples listed above a merely explanatory and are not intended to be limiting. The lid 106 may include any number of layers formed of any material including plastic, metal, wood, glass, any combination thereof, and so on. The above disclosure may also be applied to side walls or the base of the enclosure 102.

In some embodiments, the light transmissive layer 119 may be a light transmissive optical diffuser and may diffuse or scatter light emitted from the light-emitting strip 112. The light transmissive optical diffuser may also be configured to filter the emitted light so that, for example, only light in the UV-C spectrum reaches the interior cavity. The light-transmissive layer 119 may include components or features that diffuse light emitted from the light-emitting strip 112 to produce a more uniform light irradiation along the inner surface of the enclosure 102. In some cases, the light-transmissive layer 119 may include a surface texture, surface features, or other similar features that help to distribute the light produced from the light source. In some cases, the layer may include features that define a Fresnel lens or lenticular lensing features that can be used to improve the uniformity of the light irradiation. For example, optical lenses and/or diffusing layers may be used to ensure that the emitted ultraviolet light intensity is consistent throughout the interior cavity, so as to avoid hot-spots or cold-spots that would receive too much or too little light. Light-transmissive layers 119 may additionally be disposed on the lid 106 and/or on a base of the disclosure 102.

The wedge 104 may be positioned within the interior cavity of the card distribution and sanitization apparatus 100. The wedge 104 may be include a wheel or roller and may be configured to roll along the base plate of the enclosure 102. In some embodiments, the enclosure 102 may include a track (e.g., grooves) on a base plate and grooves on the wedge 104 may interact with the track so that the wedge 104 is slide-ably coupled with the enclosure 102.

The wedge 104 may be configured to receive a deck (or set) of cards and may include a top surface presented at an angle. The angle of the top surface of the wedge 104 may be substantially equivalent to the angle of the front wall 108. In alternate embodiments, the angle of the top surface of the wedge 104 may be steeper or shallower than an angle of the front wall 108. The wedge 104 may include biasing elements, such as a spring, to bias the wedge 104 forward. When a set of cards is provided on the wedge 104, the wedge 104 may be forward-biased so that the forward-most card abuts or is otherwise proximate to the front wall 108. When no cards are present on the wedge 104, the wedge 104 itself may abut or be otherwise proximate to the front wall 108. In some embodiments, the wedge 104 may be operatively coupled to a lever or wheel that that a user may manually control a position of the wedge 104 with respect to the front wall 108. In some embodiments, the wedge 104 may be operatively coupled to the battery 110 and/or an electric motor and may be mechanically moveable. The wedge 104 may be formed from any material such as a wood, a plastic, a metal, a glass, any combination thereof, and so on.

The front wall 108 may define a gap between the front wall 108 and the enclosure 102 so as to allow a card or number of cards to pass through. The gap may be referenced as an outlet and may define a space where a card moves from inside an interior cavity defined by the enclosure 102 to outside the interior cavity. The front wall 108 may additionally include a u-shaped portion (or another shaped portion) so that a user's finger may interact with a surface of a forward-most card positioned on the wedge 104 so that the card may be removed from the card distribution and sanitization apparatus 100. The front wall 108 may be formed from any material such as a wood, a plastic, a metal, a glass, any combination thereof, and so on.

The light-emitting strips 112 may include light-emitters 116, such as light-emitting diodes (LED) that transmit UV-C light having a wavelength between 200 nm and 290 nm. The LEDs may be LED chips and may be coupled to a flexible or rigid printed circuit board including resistors, electrical traces, transistors, and other electronic components. In the example illustrated in FIG. 1, three or four light-emitters 116 are provided on each light-emitting strip 112, through any number of light-emitters 116 may be provided. In some embodiments, the light-emitting strips 112 include different light-emitters emitting distinct wavelengths. For example, some light-emitters may emit visible light for user visibility while others may emit UV-C light for sanitizing cards.

The light-emitting strips 112 may all be disposed at the same angle (e.g., about 90 degrees with respect to the mounting surface) or may be disposed at different angles with respect to the mounting surface. For example, a light-emitting strip 112 may include four light-emitters 116. One light-emitter 116 may be disposed to emit light at an angle of about 15 degrees, a second light-emitter 116 may emit light at an angle of about 35 degrees, a third light-emitter may emit light at an angle of about 55 degrees, and a fourth light-emitter may emit light at an angle of about 75 degrees. In this way, nooks and crevices within the card distribution and sanitization apparatus 100 may be irradiated by light with a variety of incident angles. In some embodiments, two center light-emitters 116 may be disposed at an angle of about 90 degrees and two end light-emitters 116 may be disposed at angles of +/−about 35 degrees. The presented angles are merely for illustrative purposes and any angle of a light-emitter 116 or light-emitting strip 112 may be used.

In some embodiments, the light-emitting strips 112 may be coupled to circuitry including a timer circuit. The timer circuit may control how long the light-emitting strips 112 emit light and may automatically turn off one or a number of the light-emitting strips 112 (or LEDs thereof) when a predetermined time has passed. For example, the timer circuit may be operatively coupled to, or integrated within, a controller and may establish an exposure time where ultraviolet light irradiates an interior cavity of the card distribution and sanitization apparatus 100. The exposure time may be determined based on an intensity of the emitted ultraviolet light to result in a dosage of from about 15 mJ/cm$^2$ to 500 mJ/cm$^2$ or about 40 mJ/cm$^2$. In some embodiments, an exposure time may be multiple minutes such as, for example, about 5 minutes. In some embodiments, an exposure time may be from about 10 seconds to about 45 seconds. Once the ultraviolet light has been emitted for the length of the exposure time, the timer circuit and/or controller may shut down or otherwise prevent the light-emitting strips 112 from emitting light.

In an example operation, a dealer may place a number of cards into the card distribution and sanitization apparatus 100. Once the dealer closes the lid 106, a controller may direct the light-emitting strips 112 to begin emitting light for a period of time (e.g., a predetermined time corresponding to an exposure time). Once the period of time has passed, the controller may direct the light-emitting strips 112 to stop emitting light. Thereafter, cards may be distributed via the front wall 108. Whenever the lid 106 is reopened and closed, the operation may be reset and the controller may direct the light-emitting strips 112 to again emit light for a period of time. In addition, the switch 114 may permit the dealer or other user to manually turn on or off the light-emitting strips 112. In some embodiments, an external application (e.g., a smartphone app) may be able to wireless control operations of the card distribution and sanitization apparatus 100.

In some embodiments, a proximity sensor and/or heat sensor may act with a controller to turn on or off the light-emitting strips 112 (or LEDs thereof). In some embodiments, the light-emitting strips 112 may be an elongated tube or a bulb and may emit UV-C light via incandescent and/or LED light. As provided herein, an elongated light-emitter may refer to an elongated tube or bulb formed as an integral component. In such cases, the elongated light-emitter may be a single light-emitter. In some cases, the elongated light-emitter may refer to a group of multiple light-emitting elements (e.g., LEDs) arranged in a strip. In such cases, the elongated light-emitter may comprise a transparent housing configured to contain the multiple light-emitting elements.

A power supply 110 may be coupled to a back portion of the enclosure 102 and may be operatively coupled to each of the light-emitting strips 112 via electrical connectors. The electrical connectors may be conductive wires or other electrically transmissive element or combination of elements and may transmit power from the power supply 110 to each of the light-emitting strips 112. A switch 114 may be provided on the power supply 100 to turn the power supply 110 on or off (e.g., transmitting power or not transmitting power). The switch 114 may have two different states, an extended state when power is not being transmitted and a depressed state when power is being transmitted. In some embodiments, the switch 114 may be a lever and may indicate an activated state when positioned to one side and an inactivated state when positioned to an opposite side.

The power supply 110 may also include a battery that is configured to provide electrical power. The battery may include one or more power storage cells that are linked together to provide an internal supply of electrical power. The battery may be operatively coupled to power management circuitry that is configured to provide appropriate voltage and power levels for individual components or groups of components within card distribution and sanitization apparatus 100. The battery, via power management circuitry, may be configured to receive power from an external source, such as an AC power outlet, and may include AC/DC conversion circuitry (e.g., an AC/DC converter). The battery may store received power so that the card distribution and sanitization apparatus 100 may operate without connection to an external power source for an extended period of time, which may range from several hours to several days.

A controller may additionally be operatively coupled to, for example, the power supply 110 and/or the light-emitting strips 112. The controller may be wirelessly controllable (e.g., by a smart phone app or a remote control) and may turn on or off the power supply 110 and/or the light-emitting strips 112. In some embodiments, the controller may include timer circuitry to automatically turn on or off the power supply 110 and/or the light-emitting strips 112 after a predetermined time. In some embodiments, the controller may be operatively connected to sensors and may turn on or off the power supply 110 and/or the light-emitting strips 112 in response to sensor data.

A friction strip 113 may additionally be provided within an internal surface of the enclosure 102. The friction strip 113 may be made any material designed to apply friction to an object moving against the friction strip 113. For example, the friction strip 113 may be rubber, sandpaper, a mohair strip, and so on. In some cases, the friction strip 113 may be non-uniform such that different areas on the strip impart different frictional forces on an object in contact with the friction strip 113.

When a set of cards is present within the enclosure 102 (see FIG. 2B), the friction strip 113 may impart frictional forces to the deck of cards to separate successive cards. In this way, the friction strip 113 may cause a front and/or back face of each individual card to become illuminated by any one of the light-emitters 116. In this way, each individual card may be sanitized as sanitizing light is able to illuminate a greater surface area of each card of the deck of cards.

Figure 2A:
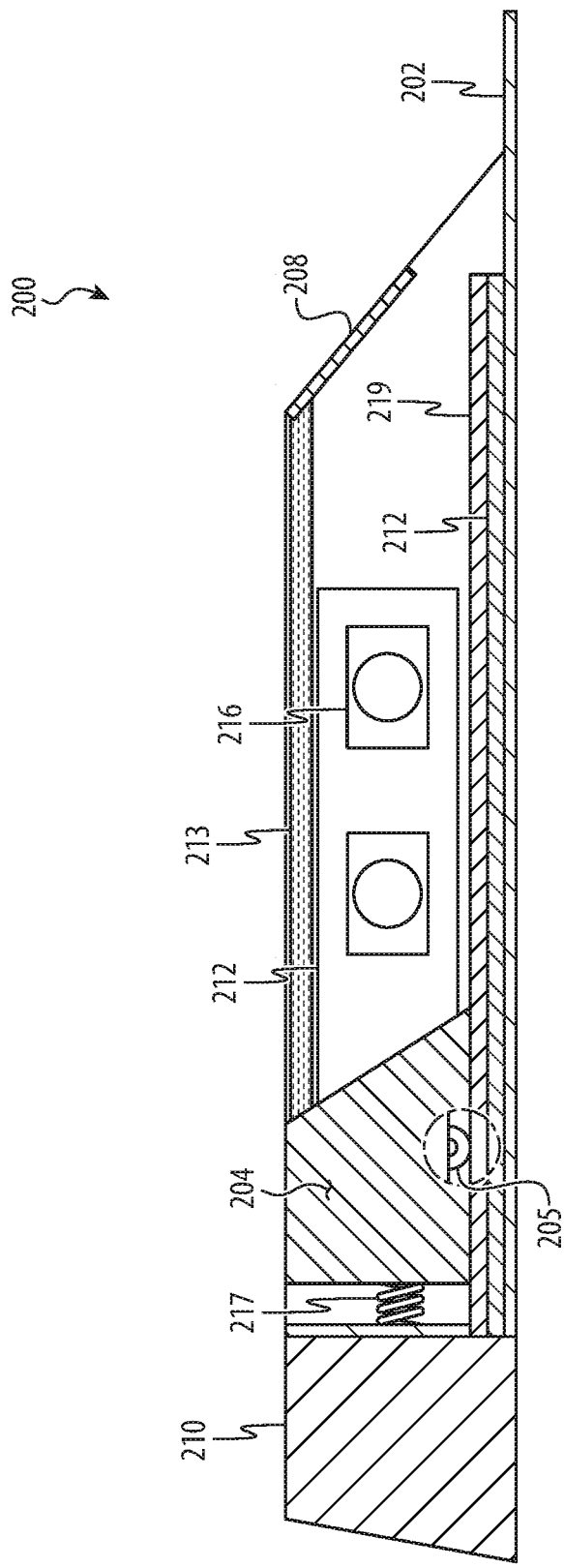
FIG. 2A depicts a cross-sectional view of an example card distribution and sanitization apparatus including multiple light-emitting elements, as described herein.

FIG. 2A illustrates a cross-sectional view of a card distribution and sanitization apparatus 200. In some embodiments, the card distribution and sanitization apparatus 200 may be equivalent to the card distribution and sanitization apparatus 100.

The card distribution and sanitization apparatus 200 may include an enclosure 202, a number of light emitting strips 212, a diffusing layer 219, light-emitters 216, a wedge 204, a wheel 205, a front wall 208, a biasing element 217, a friction strip 213, and a power supply 210.

As depicted in FIG. 2A, the wedge 204 may include a wheel 205 and may slide along a surface of the diffusing layer 219. The biasing element 217 may be operatively coupled to the wedge 204 and to the enclosure 202 and may be configured to bias the wedge 204 toward the front wall 208.

The front wall 208 may, along with a surface of the diffusing layer 219, define a gap (which may be referenced as an outlet). When cards are positioned on the wedge 204, cards may be distributed through the gap/outlet when dealt or otherwise distributed through the card distribution and sanitization apparatus 200.

The power supply 210 may be operatively coupled to the light emitting strips 212 and may be configured to provide power to the light-emitters 216. Various conductive traces and/or wires may extend from the power supply 210 and may come into contact with at least a portion of the light emitting strips 212.

A diffusing layer 219 may be positioned between the wedge 204 and the light emitting strip 212. In some embodiments, diffusing layer 219 may be an optical diffuser and may diffuse or scatter light emitted from the light-emitting strip 212. The optical diffuser may also be configured to filter the emitted light so that, for example, only light in the UV-C spectrum reaches the interior cavity. The diffusing layer 219 may be formed of an optically transparent material (e.g., a material optically transparent to UV-C light) and may be made of a glass, clear plastic, visually-opaque plastic, and so on. A similar diffusing layer may also be disposed on side walls of the enclosure 102 or on the lid 106 in front of respective light-emitting strips 112. In some embodiments, the diffusing layer 219 may be smooth to allow the wheel 205 and/or cards to smoothly slide and to be dispensed easily. In some embodiments, the diffusing layer 219 may include ridges and/or surface features to diffuse light.

Figure 2B:
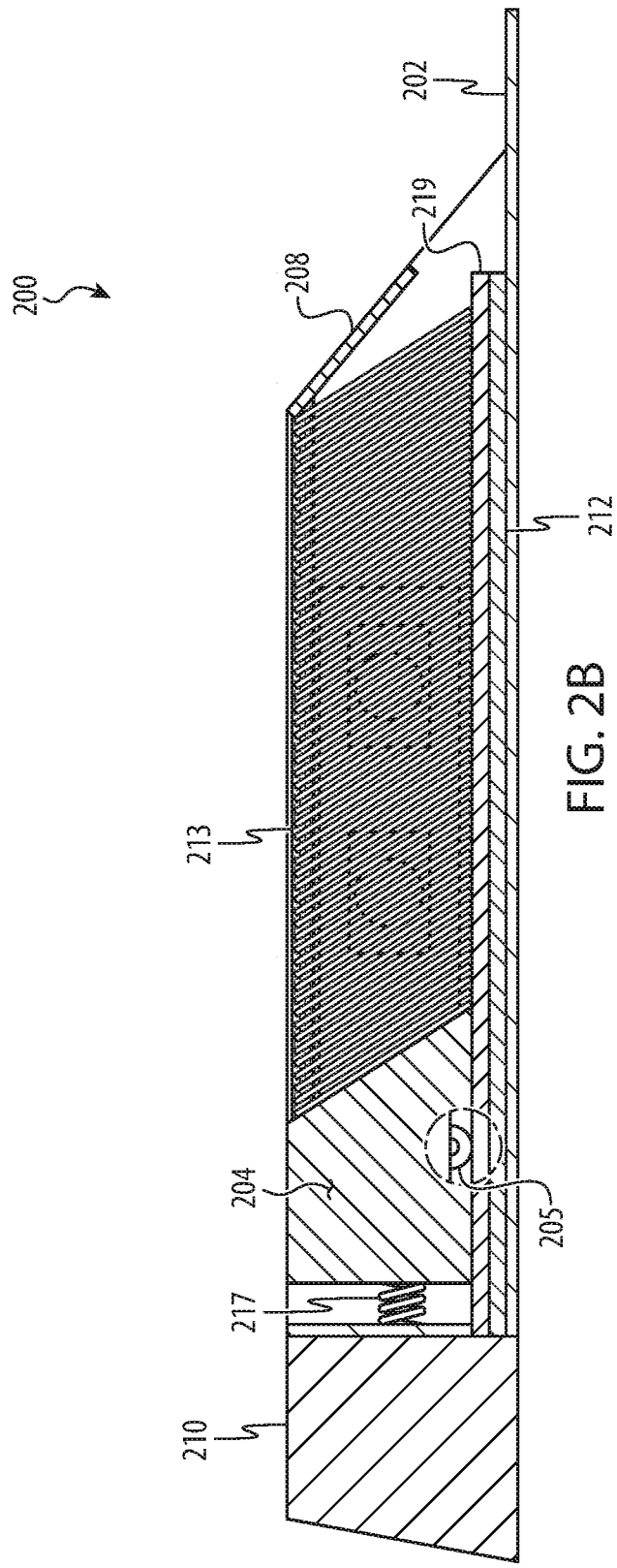
FIG. 2B depicts a cross-sectional view of an example card distribution and sanitization apparatus, including multiple light-emitting elements and a set of cards, as described herein.

FIG. 2B illustrates a cross-sectional view of an example card distribution and sanitization apparatus, including multiple light-emitting elements and a set of cards. FIG. 2B illustrates the card distribution and sanitization apparatus when a set of cards is provided in an internal cavity of the enclosure 202. As the set of cards interacts with the friction strip 213, individual cards within the set of cards may separate. For example, front and back surfaces of particular cards of the set of cards may become visible to the light-emitting strip 212. In this way, the front and back surfaces of the particular cards may be sanitized even as the cards are within the enclosure 202.

It is noted that, in FIG. 2B, each of the cards of the set of cards are spaced uniformly. While the friction strip 213 may equally space each card, this is not necessary. As the wedge 204 moves, the cards of the set of cards may become jostled, may 'stick,' or may otherwise move in a non-uniform manner. At some times, individual cards may come into contact with one another. However, as the set of cards moves through the enclosure 202, the friction strip 213 may ensure that the front and/or back portion of each card is illuminated for at least a portion of the time that each card is present within the enclosure 203. Further, there may be multiple friction strips within the enclosure 202. For example, one or more frictions strips may be provided on each wall of the enclosure.

Figure 3:
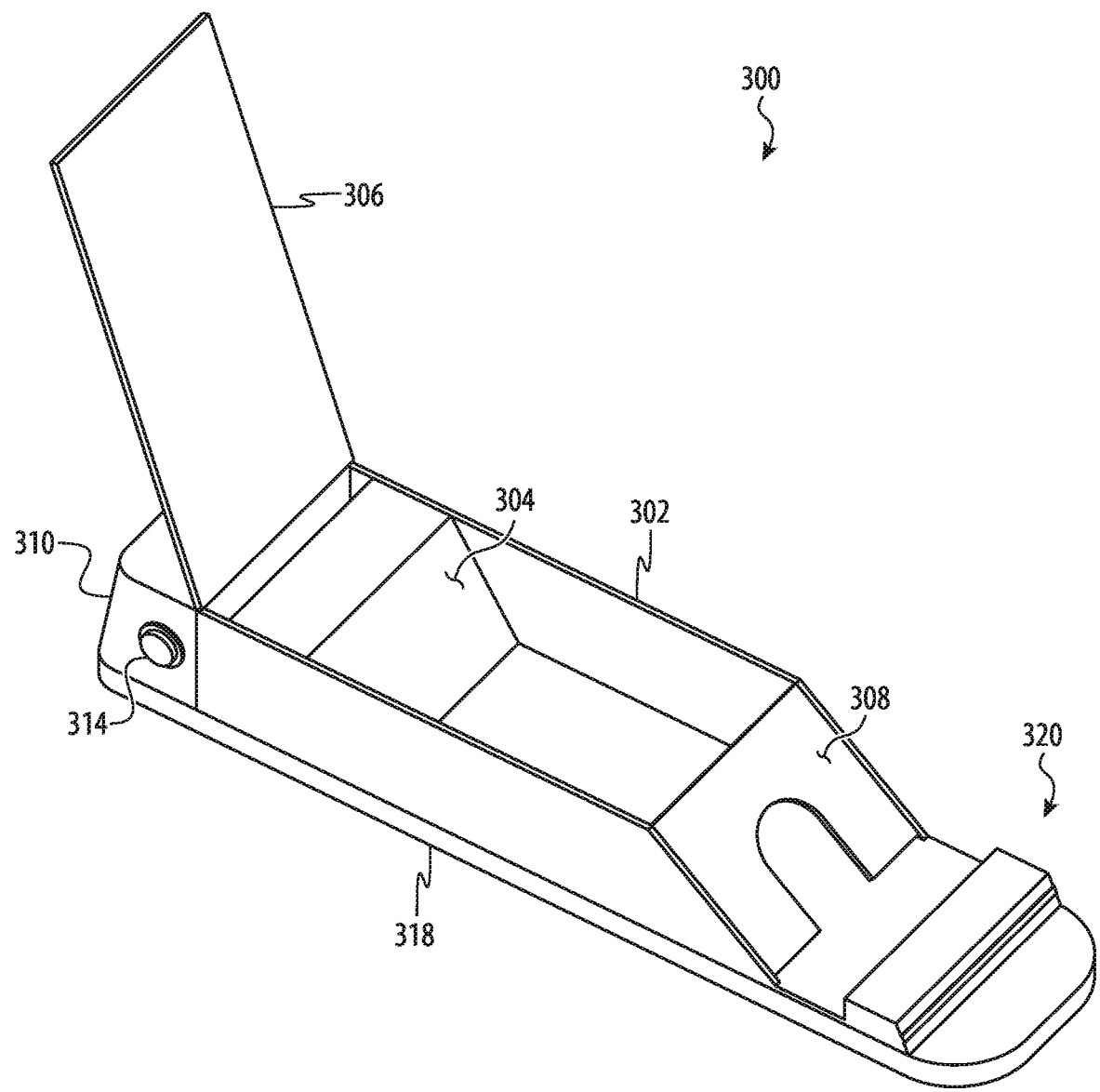
FIG. 3 depicts an example card distribution and sanitization apparatus including a light-emitting stack-up defining an outlet and a passage, as described herein.

FIG. 3 depicts an example card distribution and sanitization apparatus 300 including a light-emitting stack-up 320. As described with respect to FIGS. 1 and 2 above, the card distribution and sanitization apparatus 300 may include a housing 302, a wedge 304, a lid 306, a front wall 308, a power supply 310, and a switch 314. The operation and/or structure of these features may be the same as described above with respect to FIGS. 1 and 2.

The card distribution and sanitization apparatus 300 may additionally include a base 318 including power and signal transmission elements and a light-emitting stack-up 320. The base 318 may be fully or partially formed from a conductive material and may transmit power from the power supply 310 to the light-emitting stack-up 320. In a non-limiting example, the base 318 may include one or a number of insulated conductive wires that transmit power. In another example, the power transmission layer may be a housing formed of metal, plastic, wood, and so on and may house a number of batteries.

The light-emitting stack-up 320 may comprise an outlet surrounded by light emitting portions and diffusing portions (see, e.g., FIG. 4). As provided herein, the outlet of the light-emitting stack-up 320 may be referenced as an inlet and may be formed as a slit, space, or gap configured to permit a card to pass. After a card passes through the gap, which may be referenced as an outlet, defined by the enclosure 302 and the front wall 308, the card may pass through the outlet/inlet of the light-emitting stack-up 320 and may be sanitized by UV-C light emitted from portions of the light-emitting stack-up.

Figure 4A:
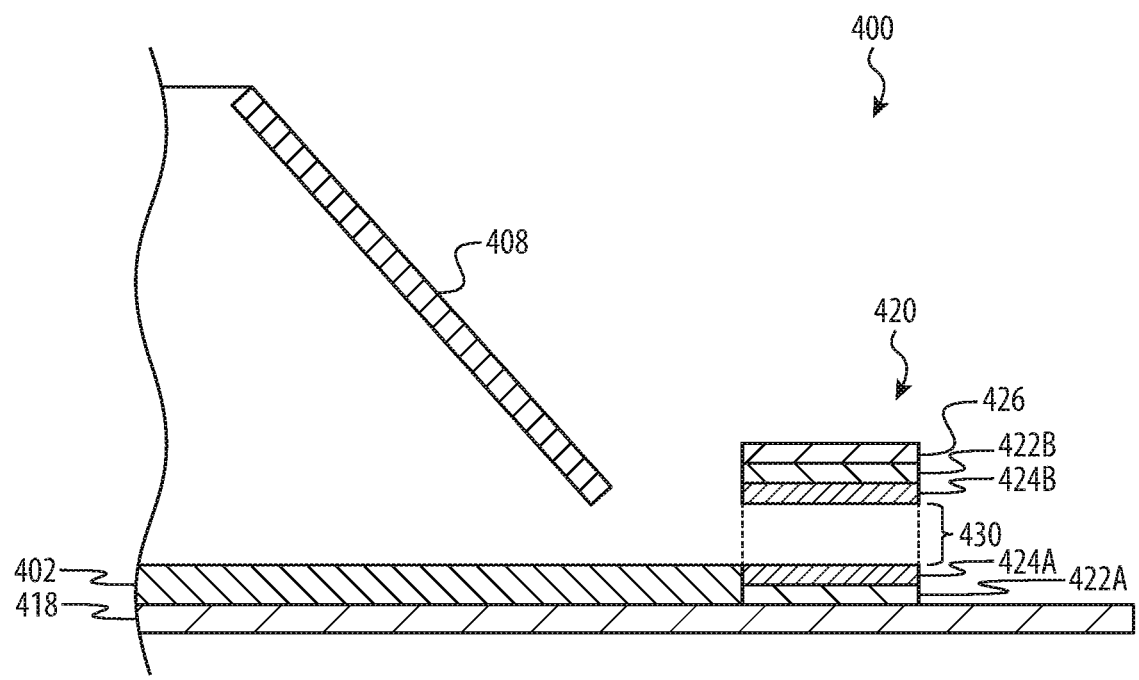
FIG. 4A depicts a cross-sectional view of a light-emitting stack-up defining an outlet and a passage of an example card distribution and sanitization apparatus, as described herein.
Figure 4B:
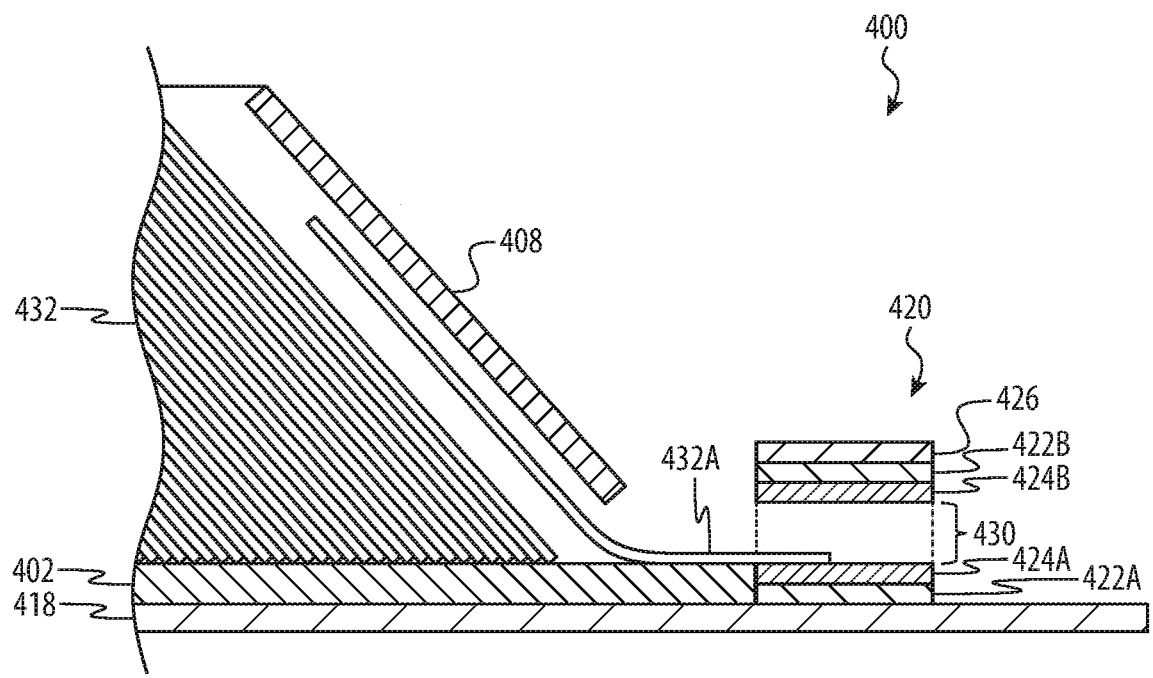
FIG. 4B depicts the cross-sectional view of FIG. 4A while a card of a set of cards passes through an outlet and a passage of an example card distribution and sanitization apparatus, as described herein.

FIGS. 4A and 4B depict a partial cross-sectional view of a card distribution and sanitization apparatus 400. In some embodiments, the card distribution and sanitization apparatus 400 may correspond to the card distribution and sanitization apparatus 300.

As depicted in FIG. 4A, a top wall 408 and an enclosure 402 may define a gap for a card to pass through. A light-emitting stack-up 420 may further define an outlet/inlet 430 for the card to pass through after passing through the gap. The light-emitting stack-up 420 may additionally comprise a passage comprising a certain length. As used herein, the outlet/inlet 430 may refer to an opening and the passage may refer to an end-to-end length that a card passes through. The light-emitting stack-up 420 may further include a first light-emitter 422A, a first diffusing layer 424A, a second light-emitter 422B, a second light-emitter 424B, and an upper housing 426. The upper housing 426 may be a housing configured to wrap around an external surface of the light-emitting stack-up 420 and may be formed of the same or different material as enclosure 402.

The first light-emitter 422A and the second light-emitter 422B may be UV-C emitting LEDs, light-emitting strips, fluorescent tubes, halogen lights, CFL (compact fluorescent lamp) light, light transmit through a waveguide or light pipe, gas or pellet lamps, incandescent bulbs, or any other UV-C light-emitter. Power to operate the first and second light-emitters 422A and 422B may be transmit by the base layer 418 including power transmission elements. For example, wires or conductive traces may travel through the housing 426 and may operatively couple end portions of the first and second light-emitters 422A and 422B to each other and to the base layer 418. The first and second light-emitters 422A and 422B may be independently controllable, in some embodiments, or may operate as one light-emitting element. As described herein, the first light-emitter 422A and the second light-emitter 422B may be positioned on either side of the light-emitting stack-up 420 such that a passage is formed between the first light-emitter 422A and the second light-emitter 422B. In other words, the first light-emitter 422A and the second light-emitter 422B may be positioned on opposing sides of the passage.

The first diffusing layer 424A and the second diffusing layer 424B may act to diffuse and/or scatter light emitted from the first and second light-emitters 422A and 422B and may act as a guide layer to guide a card through the outlet 430. The first and second diffusing layers 424A and 424B may be at least partially optically transparent in the UV-C spectrum range and may permit the passage of light emitted from the first and second light-emitters 422A and 422B. The first and second diffusing layers 424A and 424B may be formed of, for example, an optically transparent material in the UV-C spectrum such as glass or plastic. The first and second diffusing layers may include components or features that diffuse light emitted from the first and second light-emitters to produce a more uniform light irradiation along the area defined by the outlet 430. In some cases, the first and second diffusing layers may include a surface texture, surface features, or other similar features that help to distribute the light produced from the light source. In some cases, the layers may include features that define a Fresnel lens or lenticular lensing features that can be used to improve the uniformity of the light irradiation. For example, optical lenses and/or diffusing layers may be used to ensure that the emitted ultraviolet light intensity is consistent throughout the area defined by the outlet 430, so as to avoid hot-spots or cold-spots that would otherwise receive too much or too little light. The first and second diffusing layers may also include surface feature and/or grooves to guide a card through the outlet 430. In some embodiments, the first and second diffusing layers may be smooth to permit the card to smoothly move through the outlet 430.

A controller may be operatively coupled to the first and second light-emitters 422A and 422B and may control an intensity and/or emission time of the first and second light-emitters. 422A and 422B. In some embodiments, both of the light-emitters may emit UV-C light at between 1,000 mW to 10 mW which, over an area of a squared centimeter, may correspond to an intensity of 1,000 $mW/cm^2$ to 10 $mW/cm^2$. For each of the first and second light-emitters 422A and 422B, multiple, for example, LED diodes emitting UV-C light at between 1,000 mW to 10 mW may be provided to an area from 6 $cm^2$ to 24 $cm^2$ to result in an intensity of between about 250 $mW/cm^2$ to about 0.4 $mW/cm^2$.

FIG. 4B illustrates an example of one card 432A of a deck of cards 432 moving through the light-emitting outlet 420. In some embodiments, a card 432A may move through the outlet 430 for a period of time from about 1 second to 10 seconds. As the length of the light-emitting stack-up 430 may be shorter than a length of the card 432A, each region of the card 432A may be within the light-emitting stack-up 430 for 0.1 seconds to 1 second. Based on the predicted time that a portion of a card spends within the light-emitting stack-up 430, a desired intensity may be selected to reach a threshold dosage. The above values are explanatory only and any card speed value may be used in accordance with the disclosure.

In some embodiments, a threshold dosage may be about 10 $mJ/cm^2$ to about 500 $mJ/cm^2$ or may be about 40 $mJ/cm^2$. In some embodiments, an intensity value of the first and second light-emitters 422A and 422B may be set to about 40 $mW/cm^2$ to reach the threshold dosage when each portion of a card 432A spends about 1 second within the light-emitting stack-up 420. If a portion of the card 432A spends about 0.1 seconds within the light emitting stack-up 420, a desired intensity value may be about 400 $mW/cm^2$.

The above values are merely explanatory and any intensity, area, or time value may be used to calculate a proper UV-C dosage. In some embodiments, the light-emitting stack-up 420 may be substantially equivalent in length as the card 432A, which may result in a lower intensity value.

Figure 5:
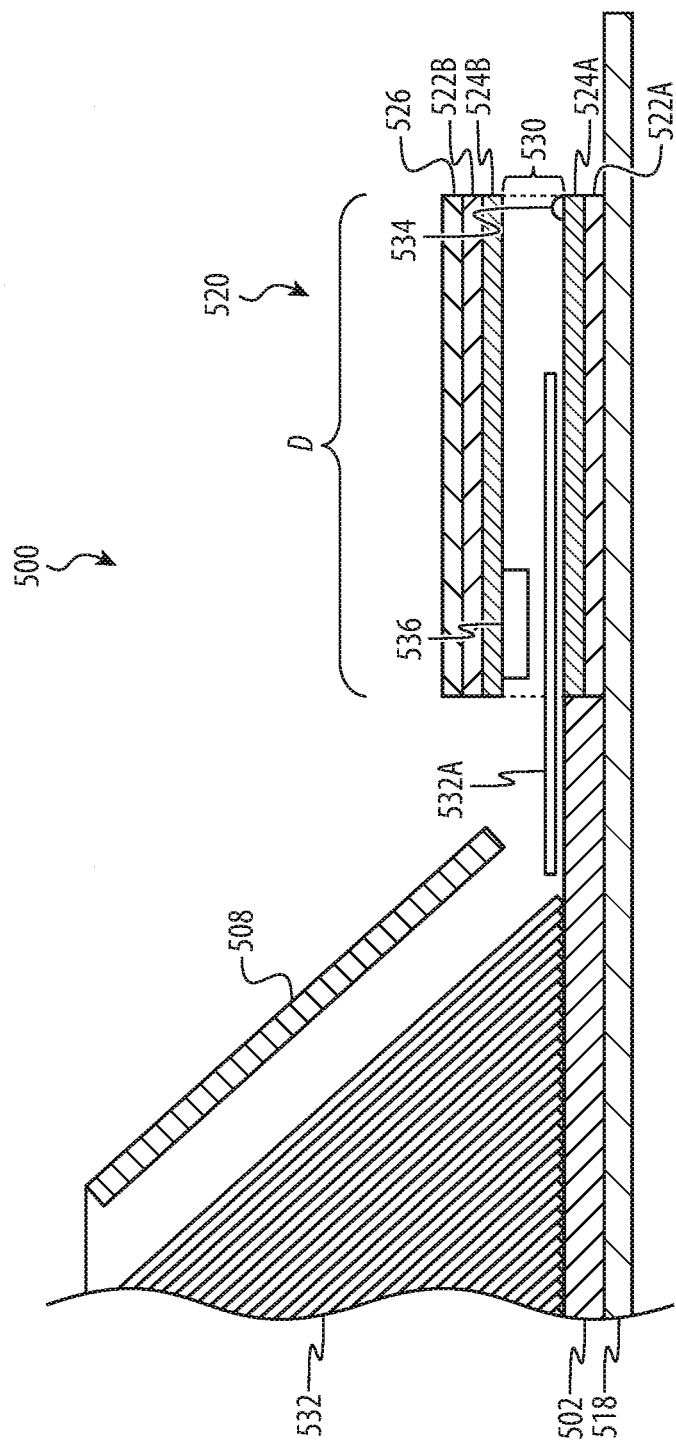
FIG. 5 depicts a cross-sectional view of an example card distribution and sanitization apparatus including a light-emitting stack-up having an elongated length, as described herein.

FIG. 5 illustrates a cross-section of a card distribution and sanitization apparatus 500 when the light-emitting stack-up 520 has a length D that is substantially equivalent to a length of a card 532. As depicted in FIG. 5, a card distribution and sanitization apparatus 500 may include a front wall 508, an enclosure 502, and a base layer 518. These elements may be substantially similar to those discussed with respect to FIGS. 4A and 4B. The enclosure may hold a deck of cards 532 including a card 532A.

The light-emitting stack-up 520 may have a length D that may be approximately 89 mm long. In some embodiments, the length D may be about 10 centimeters, though any length for D may be used in accordance with the provided disclosure. Similarly to the embodiment described with respect the FIGS. 4A and 4B, the light-emitting stack-up 520 may include a first light-emitter 522A, a first diffusing layer 524A, a second light-emitter 522B, a second light-emitter 524B, and an upper housing 526. The light-emitting stack-up 520 may further define a gap 530.

The first and second diffusing layers may include components or features that diffuse light emitted from the first and second light-emitters to produce a more uniform light irradiation along the area defined by the outlet 530. In some cases, the first and second diffusing layers may include a surface texture, surface features, or other similar features that help to distribute the light produced from the light source. In some cases, the layers may include features that define a Fresnel lens or lenticular lensing features that can be used to improve the uniformity of the light irradiation. For example, optical lenses and/or diffusing layers may be used to ensure that the emitted ultraviolet light intensity is consistent throughout the area defined by the outlet 530, so as to avoid hot-spots or cold-spots that would otherwise receive too much or too little light. The first and second diffusing layers may include surface features and/or may be smooth to guide and/or allow a card to smoothly move through the outlet 530.

In addition, a protrusion 534 may be provided along an interior surface of the light-emitting stack-up 520. The protrusion 534 may be a bump formed from any material and may inhibit a forward progress of the card 532A as the card 532A reaches an end of the light-emitting stack-up 520. If the card 532A has a sufficient momentum, the card 532A may rise above the protrusion 534 and may continue past the light-emitting stack-up 520.

In some embodiments, the protrusion 534 may be coupled to the base layer 518 and may be actively controlled. The protrusion 534 may be extendable and depressible. For example, the protrusion 534 may be operatively coupled to the proximity sensor 536 and may be extended once the proximity sensor 536 detects the presence of a card 532A at the outlet 530. The protrusion 534 may remain extended, thereby preventing the card 532A from exiting the outlet, until a sufficient dosage is determined to have been imparted to the card 532A. For example, an exposure time may be measured and the protrusion 534 may be extended during the entirety of the exposure time. Once the exposure time has concluded, a controller may direct the protrusion 534 to depress and allow the card 532A to move through the outlet 530.

A proximity sensor 536 may also be provided. The proximity sensor 536 may be configured to detect the presence or movement of an object with the light-emitting stack-up 520. For example, the proximity sensor 536 may be an infrared emitter and receiver pair and may emit infrared light and may determine the presence of an object based on the infrared light received at the receiver. The proximity sensor 536 may also be an ambient light detector and may product a detection signal when an ambient light within the light-emitting stack-up 520 changes. In some embodiments, the proximity sensor 536 may be a camera and may use image analysis to determine the presence of a card (e.g., card 532A). The proximity sensor 536 may be operatively coupled to a controller of the card distribution and sanitization device 500 and operations of the light-emitters may be controlled as a result of a generated detection signal. The proximity sensor 536 may be positioned on a side wall of the light-emitting stack-up 520 and/or may be positioned on a top or bottom wall.

As the length D of the light-emitting stack-up 520 is longer than the embodiment depicted in FIGS. 4A and 4B, the exposure time may be lower than the above described embodiment. The light-emitting stack-up 520 may additionally include a, for example, u-shaped hole so that a user may remove the card 532A from the light-emitting stack-up 520.

Figure 6:
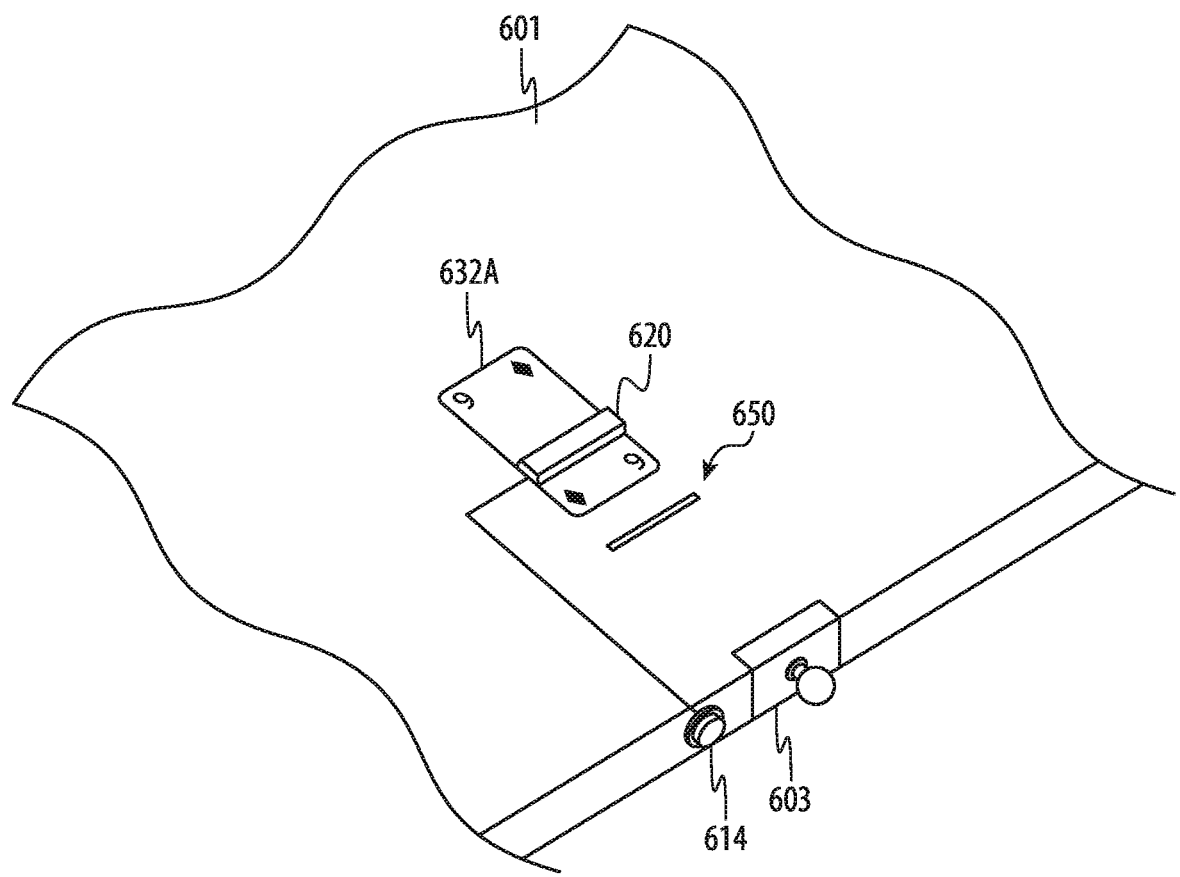
FIG. 6 depicts an example card distribution and sanitization apparatus integrated into a table including a surface for a card game, as described herein.

FIG. 6 illustrates a light-emitting stack-up 620 when installed on a surface of a table 601 (e.g., a table for playing a card game). A drawer 603 may additionally be provided to hold a card or a deck of cards and may be communicatively coupled to a slit 650. A ramp may be provided underneath the slit 650 so that cards installed within the drawer 603 may be distributed through the slit 650. The drawer 603 may be moveable in both directions with respect to the table 601 (e.g., in a push-in direction and a push-out direction) and may be used to distribute additional cards (e.g., when pushed-in) and/or to replace cards (e.g., when pulled-out. A switch 614 operatively coupled with the light-emitting stack-up 620 may additionally be provided to control when light-emitters of the light-emitting stack-up 620 turn on or off. In some embodiments, a length of the light-emitting stack-up 620 may be approximately a length of the card 632A.

As depicted in FIG. 6, a light-emitting stack-up 620 may be placed on a surface of the table 601 and may guide a card 632A after the card 632A moves through the slit 650. In this way, the card 632A may be provided to a top surface of the table 601 for use in a card game.

The light-emitting stack-up 620 may operate in a substantially similar manner as described with respect to FIGS. 1-4B. For example, the light-emitting stack-up 620 may include light-emitters, diffusing layers, and a proximity sensor and may emit ultraviolet light for a certain period of time after a card 632A is detected. In some embodiments, the light-emitting stack-up 620 may be operated manually by the switch 614. For example, a user may turn the light-emitting stack-up 620 on or off via the switch 614. The dosage applied to the card 632A by the light-emitting stack-up 620 may be between about 10 mJ/cm$^2$ and about 500 mJ/cm$^2$ and may be about 40 mJ/cm$^2$.

Figure 7:
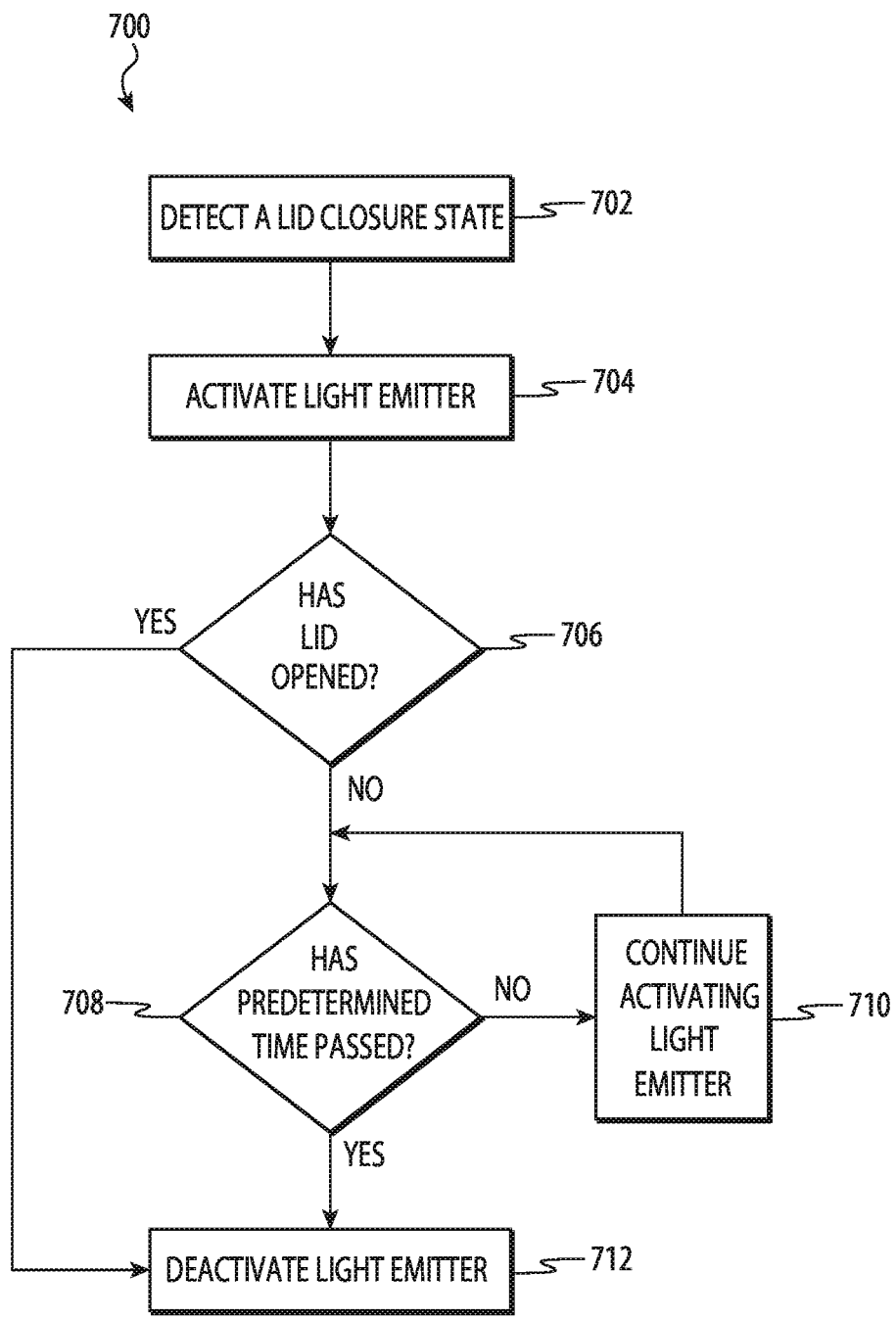
FIG. 7 depicts a flowchart for a process for initiating and stopping the emission of ultraviolet light based on the state of a lid of an example card distribution and sanitization apparatus, as described herein.

FIG. 7 depicts a process 700 for sanitizing an interior cavity of a card distribution and sanitization apparatus. At operation 702, a lid closure state of the card distribution and sanitization apparatus is detected. In some embodiments, a contact switch may be provided proximate to a lid. The contact switch may be depressed by the lid when the lid is closed but may be extended when the lid is open. Magnetic switches may also be provided with a magnet disposed within the lid portion and a magnetic sensor disposed within an enclosure. Any manner of detecting a lid closure state may be utilized in accordance with the provided disclosure.

At operation 704, ultraviolet light (e.g., UV-C light) may be emitted after the lid closure state is detected at operation 702. The ultraviolet light may be emitted automatically as soon as the lid closure state is detected at operation 702 or may be emitted after a user engages with a switch or button. The ultraviolet light may be emitted at a stable intensity or may transition between a range of intensities.

The dosage applied to a card by the ultraviolet light may be selected based on experimental values for removing contaminants from a surface of a card. The desired dosage to remove a substantial portion of the contaminants may be referred to as a threshold dosage. The threshold dosage may be selected based on an intensity of emitted ultraviolet light and/or on a desired emission time. For example, a threshold dosage may be about 10 mJ/cm$^2$ to about 500 mJ/cm$^2$ or may be about 40 mJ/cm$^2$. In some embodiments, an intensity value of ultraviolet emitters may be set to about 4 mW/cm$^2$ to reach the threshold dosage when a card or deck of cards spends about 10 seconds within a card distribution and sanitization apparatus. In some embodiments, a desirable dosage may be set higher (e.g., 500 mJ/cm$^2$) and an exposure time may be set above a minimum exposure time. For example, an exposure time may be set to be about 1 minute and an intensity value of a light-emitter may be set to be about 5 mW/cm$^2$ through about 50 mW/cm$^2$. In this way, an applied dosage may successfully irradiate a surface based on predetermined parameters.

At operation 706, a lid status is determined. If the lid has opened at operation 706, then the ultraviolet light may be automatically turned off to avoid coming into contact with a user. If the lid is not opened at operation 706, then a controller may determine, via a clock or timer, whether a predetermined time has passed. A predetermined time may be selected based on anticipated damage to a deck of cards based on ultraviolet light exposure. For example, a period of 30 seconds may be considered sufficient to sanitize a deck of cards without causing any damage. The predetermined time of 30 seconds is merely one example and any time period may be used.

If the predetermined time period has not passed at operation 708, the ultraviolet light may continue being emitted at operation 710. The predetermined time period may be periodically queried for as long as ultraviolet light is being emitted. When the predetermined time period has passed, the ultraviolet light may be turned off at operation 712.

Figure 8:
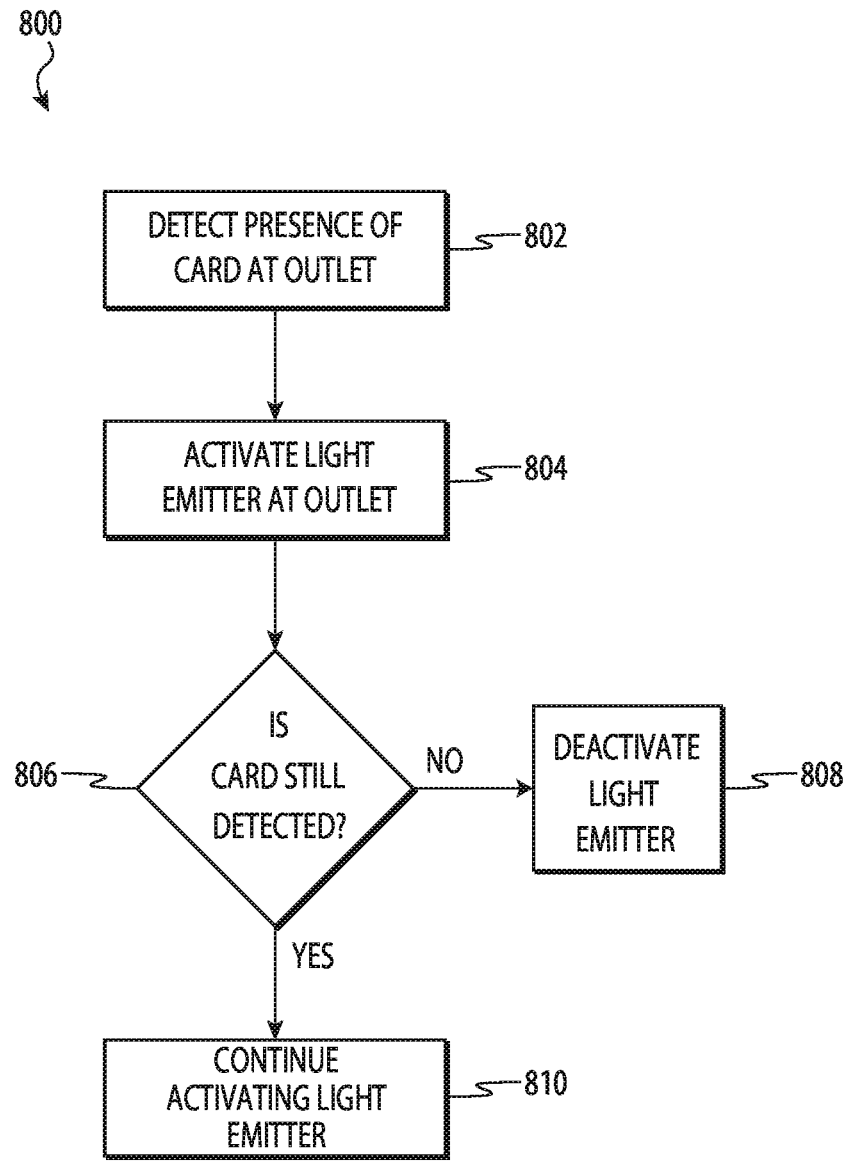
FIG. 8 depicts a flowchart for a process for initiating and stopping the emission of ultraviolet light based on a detection of a presence of a card at an outlet of an example card distribution and sanitization apparatus, as described herein.

FIG. 8 depicts a process 800 for sanitizing an outlet of a card distribution and sanitization apparatus in response to a presence detection. At operation 802, a card may be detected at an outlet of the card distribution and sanitization apparatus. For example, a proximity sensor may be directed toward the outlet and may detect the presence of the card by, for example, different in ambient light and/or difference in reflected light. In some embodiments, a proximity sensor may be a mechanical switch that is depressed as a card comes into contact with the mechanical switch and reverts when the card is removed. Any manner of detecting the presence of a card may be utilized in accordance with the provided disclosure.

At operation 804, ultraviolet light (e.g., UV-C light) may be emitted after the presence of the card is detected at operation 802. The ultraviolet light may be emitted automatically as soon as the proximity of the card is detected at operation 802 or may be emitted after a user engages with a switch or button. The ultraviolet light may be emitted at a stable intensity or may transition between a range of intensities. In some embodiments, a light-emitter may emit ultraviolet light for as long as a presence of a card is detected at operation 802.

In alternate or additional embodiments, the dosage applied to a card by the ultraviolet light may be selected based on experimental values for removing contaminants from a surface of a card. The desired dosage to remove a substantial portion of the contaminants may be referred to as a threshold dosage. With respect to the process described in FIG. 7, the operation 804 may include light-emitters emitting ultraviolet light with a higher intensity to account for a possible decrease in exposure time. The threshold dosage may be selected based on an intensity of emitted ultraviolet light and/or on a desired emission time. For example, a threshold dosage may be about 10 mJ/cm$^2$ to about 500 mJ/cm$^2$ or may be about 40 mJ/cm$^2$. In some embodiments, an intensity value of ultraviolet emitters may be set to about 40 mW/cm$^2$ to reach the threshold dosage when each portion of a card spends about 1 seconds within a card distribution and sanitization apparatus. In some embodiments, a desirable dosage may be set higher (e.g., 500 mJ/cm$^2$) and an exposure time may be estimated to be lower. For example, an exposure time may be set to be about 0.1 seconds and an intensity value of a light-emitter may be set to be about 300 mW/cm$^2$ through about 500 mW/cm$^2$. In this way, an applied dosage may successfully irradiate a surface based on predetermined parameters.

At operation 806, a continuing presence of the card is determined. If the card is no longer present at operation 806, then the ultraviolet light may be automatically turned off to avoid excessive power use at operation 808. If the card is still present at operation 806, then ultraviolet light may continue being emitted at operation 810. In some embodiments, operation 810 may revert to operation 806 to continuously query whether a card is present at an outlet while ultraviolet light is being emitted.

In some embodiments, an automated shutoff switch may turn off the ultraviolet light even if the card is still detected at operation 806. The automated shutoff switch may be initiated after a predetermined time as passed to avoid causing UV-C-caused damage to the card.

If the predetermined time period has not passed at operation 808, the ultraviolet light may continue being emitted at operation 810. The predetermined time period may be periodically queried for as long as ultraviolet light is being emitted. When the predetermined time period has passed, the ultraviolet light may be turned off at operation 812.

Figure 9:
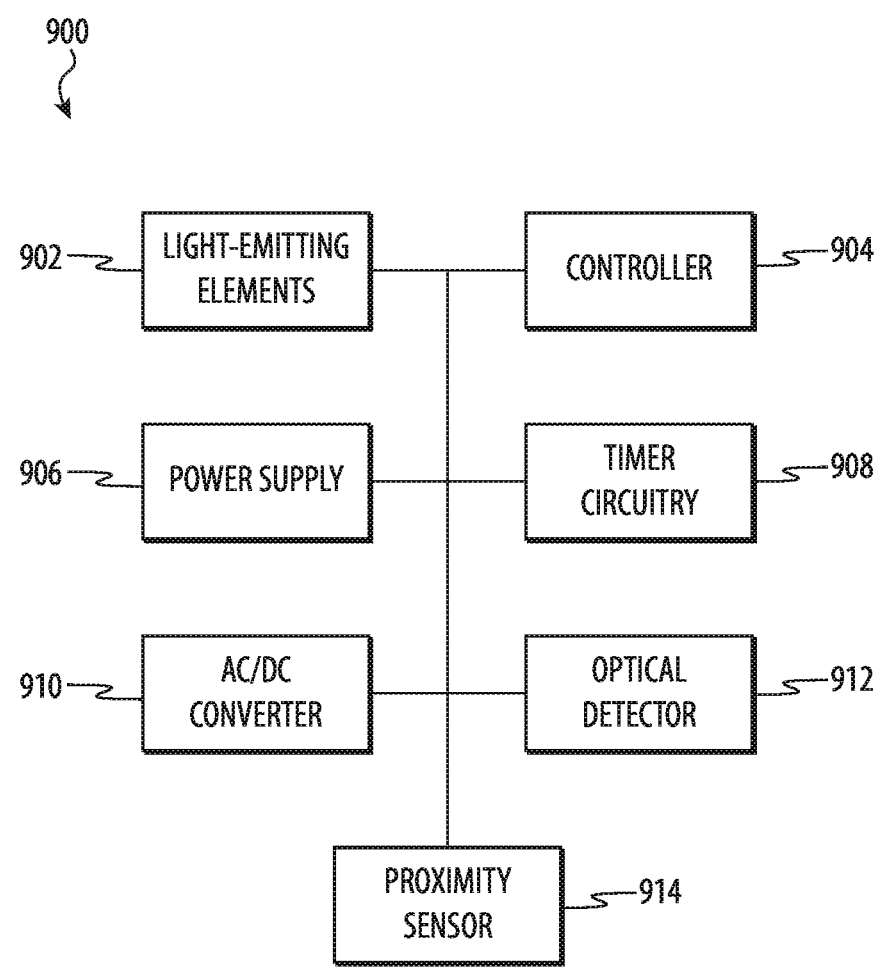
FIG. 9 depicts a block diagram of electrical systems of an example card distribution and sanitization apparatus, as described herein.

FIG. 9 depicts an example card distribution and sanitization apparatus 900 including a number of electrical elements, such as discussed with respect to FIGS. 1-8. The card distribution and sanitization apparatus 900 is only one such example and other assemblies in accordance with the provided disclosure are considered. For example, additional or fewer elements may be provided in additional or alternative apparatuses.

In embodiments, a card distribution and sanitization apparatus 900 may include light-emitting elements 902. As discussed throughout the specification, the light-emitting elements may be configured to emit ultraviolet light (e.g., UV-C) light. The light-emitting elements 902 may be coupled to an additional electrical element, such as a flexible or rigid printed circuit board, and may be powered by a power supply (e.g., power supply 906). The light-emitting elements 902 may be light-emitting diodes (LEDs), elongated lamps, light-emitting tubes, incandescent bulbs, bulb-shaped light-emitters, any combination thereof, and so on. Any light-emitter, and associated structures including sleeves (e.g., quartz sleeves), mercury drops, insulating material, and so on, that may emit ultraviolet light having a wavelength between about 10 nm and about 400 nm may be used in accordance with the provided disclosure.

The card distribution and sanitization apparatus 900 may also include a controller 904 operably connected with an electrical system of the card distribution and sanitization apparatus 900. The controller 904 may be implemented as one or more computer processors or microcontrollers configured to perform operations in response to computer-readable instructions and may communicate with a variety of types of non-transitory computer-readable storage media.

The controller 904 may include a central processing unit (CPU) of the card distribution and sanitization apparatus 900. Additionally, and/or alternatively, the controller 904 may include other electronic circuitry within the card distribution and sanitization apparatus 900 including application specific integrated chips (ASIC) and other microcontroller devices. The controller 904 may be configured to perform functionality described in the examples above. For example, the controller 904 may be coupled to any number of light-emitting elements 902, timer circuitry 908, optical detector 912, proximity sensor 914, and so on, and may control any associated operations. For example, the controller 904 may control the light-emitting elements 902 so as to emit, begin emitting, or stop emitting light. Such operations may occur in response to a signal from, for example, proximity sensor 914 so that light-emitting elements 902 are operated when a movement is detected (e.g., a card movement).

The card distribution and sanitization apparatus 900 may also include a power supply 906. The power supply 906 may include a battery that is configured to provide electrical power. The battery may include one or more power storage cells that are linked together to provide an internal supply of electrical power. In some cases, the battery may be operatively coupled to power management circuitry that is configured to provide appropriate voltage and power levels for individual components or groups of components within the card distribution and sanitization apparatus 900. The battery, via power management circuitry, may be configured to receive power from an external source, such as an AC power outlet, and may include AC/DC conversion circuitry (e.g., an AC/DC converter 910). The battery may store received power so that the card distribution and sanitization apparatus 900 may operate without connection to an external power source for an extended period of time, which may range from several hours to several days.

In some cases, the power supply 906 may be a power supply connected to, for example, a wall outlet. Any power supply 906 configured to provide power to the card distribution and sanitization apparatus 900 may be used in accordance with the provided disclosure.

The card distribution and sanitization apparatus 900 may additionally include timer circuitry 908. The timer circuitry 908 may be a part of the controller 904 or may exist as separate circuitry including resistors, capacitors, and so on. The timer circuitry 908 may additionally be coupled to the light-emitting elements 902 and may, along with the controller 904, cause the light-emitting elements 902 to begin or stop emitting light. The timer may include a counter (e.g., a countdown counter) that is initially set to a predetermined time (e.g., 3 seconds). The predetermined time may begin counting down after an event is detected, such as a card movement via the proximity sensor 914. At the beginning of the predetermined time, the light-emitting elements 902 may be turned on. After the predetermined time has elapsed, as determined through the user of the timer circuitry 908, the light-emitting elements 902 may be turned off. In this way, the light-emitting elements 902 may be controlled so as to reduce extraneous emission of light.

As discussed with respect to the power supply 906, an alternating-current-to-direct-current (AC/DC) converter 910 may additionally be provided. The AC/DC converter 910 may be any time of converter that converts alternating current to direct current and may include, for example, rectifiers, power supply units, rotary converters, switched-mode power supplies, and so on. The AC/DC converter 910 may convert power (e.g., utility power) as received from, for example, a wall outlet into a form usable by the card distribution and sanitization apparatus 900. In some cases, the AC/DC converter 910 may be omitted if, for example, the card distribution and sanitization apparatus is powered by a battery or other form of power supply 906.

An optical detector 912 may additionally be provided. As discussed herein, the optical detector 912 may be configured to sense an intensity and/or dosage of light emitted by light-emitting elements 902. The optical detector 912 may be any kind of optical detector configured to detect light intensity and/or dosage. For example, the optical detector 912 may be a photodiode and may convert received light into a measurable current. In some examples, a charge coupled device (CCD) may be used to convert light to an output voltage. The particular type of optical detector 912 is not limited and any device configured to detect light may be used in accordance with the provided disclosure. The optical detector 912 may be operatively coupled to the controller 904 and the controller 904 may, in turn, control operations of the light-emitting elements 902 in accordance with signals from the optical detector 912.

A proximity sensor 914 may additionally be included within the card distribution and sanitization apparatus 900. The proximity sensor 914 may be configured to detect the presence or movement of an object with the card distribution and sanitization apparatus 900. For example, the proximity sensor 914 may be an infrared emitter and receiver pair and may emit infrared light and may determine the presence of an object based on the infrared light received at the receiver. The proximity sensor 914 may additionally or alternatively be an ambient light detector and may product a detection signal when an ambient light within the card distribution and sanitization apparatus 900 changes. In some embodiments, the proximity sensor 914 may be a camera and may use image analysis to determine the presence of a card. The proximity sensor 914 may be operatively coupled to a controller 904 of the card distribution and sanitization device 900 and operations of the light-emitters may be controlled as a result of a generated detection signal.

Other examples and implementations are within the scope and spirit of the disclosure and appended claims. For example, features implementing functions may also be physically located at various positions, including being distributed such that portions of functions are implemented at different physical locations. Also, as used herein, including in the claims, "or" as used in a list of items prefaced by "at least one of" indicates a disjunctive list such that, for example, a list of "at least one of A, B, or C" means A or B or C or AB or AC or BC or ABC (i.e., A and B and C). Further, the term "exemplary" does not mean that the described example is preferred or better than other examples.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art that many modifications and variations are possible in view of the above teachings.

What is claimed is:

1. A card distribution and sanitization apparatus for disinfecting a set of cards, the apparatus comprising:
    a power supply;
    an enclosure defining an interior cavity configured to support the set of cards, the enclosure comprising a front wall defining a gap configured to allow a card of the set of cards to be removed from the interior cavity;
    a card sanitizing stack-up coupled to the enclosure and defining an outlet configured to receive the card of the set of cards after the card passes through the gap, the card sanitizing stack-up comprising:
        a first light-emitter operably coupled to the power supply, the first light-emitter configured to emit light toward a first side of the card as the card moves through the outlet;
        a first optical diffuser coupled to the first light-emitter and configured to distribute light emitted from the first light-emitter to the first side of the card;
        a second light-emitter separated from the first light-emitter by at least the outlet and operably coupled to the power supply, the second light-emitter configured to emit light toward a second side of the card as the card moves through the outlet, the second side of the card opposite from the first side of the card; and
        a second optical diffuser coupled to the second light-emitter and configured to distribute light emitted from the second light-emitter to the second side of the card; and
    a controller operably coupled to the power supply and configured to control the first light-emitter and the second light-emitter to disinfect both the first side and the second side of the card as the card passes through the outlet.

2. The card distribution and sanitization apparatus of claim 1, wherein:
    the enclosure comprises:
        a base plate;
        a first side wall extending from a first end of the base plate; and
        a second side wall extending from a second end of the base plate, the first end opposite from the second end;
    the front wall is coupled to the first side wall and the second side wall;
    the base plate, the first side wall, the second side wall, and the front wall define the interior cavity; and
    the base plate is coupled to the card sanitizing stack-up outside of the interior cavity.

3. The card distribution and sanitization apparatus of claim 1, wherein:
    light emitted by both the first light-emitter and the second light-emitter has a wavelength between 200 nm and 290 nm; and
    the controller is configured to operate the first light-emitter and the second light-emitter at a duration to cause at least a portion of microorganisms present on a surface of the card to be ruptured.

4. The card distribution and sanitization apparatus of claim 3, wherein at least one of the first optical diffuser or the second optical diffuser physically guides the card as the card passes through the outlet such that the card is in contact with the at least one of the first optical diffuser or the second optical diffuser.

5. The card distribution and sanitization apparatus of claim 1, further comprising a proximity sensor configured to detect a presence of the card at the outlet.

6. The card distribution and sanitization apparatus of claim 5, wherein the controller directs at least one of the first light-emitter or the second light-emitter to begin emitting light after the proximity sensor detects the presence of the card at the outlet.

7. The card distribution and sanitization apparatus of claim 5, wherein the controller increases an intensity of light emitted by at least one of the first light-emitter or the second light-emitter after the proximity sensor detects the presence of the card at the outlet.

8. A card distribution and sanitization apparatus comprising:
a housing defining:
an interior cavity configured to support a set of cards; and
an outlet for a card of the set of cards to pass through, the outlet positioned at a front portion of the housing;
a light-emitting stack-up positioned proximate to the outlet and defining an inlet for receiving the card, the light-emitting stack-up comprising:
a first light-emitter configured to emit light toward the card as the card passes through the light-emitting stack-up; and
a second light-emitter configured to emit light toward the card as the card passes through the light-emitting stack-up, the first light-emitter and the second light-emitter separated by a passage of the light-emitting stack-up; and
a controller operatively coupled to the first light-emitter and the second light-emitter and configured to operate the first light-emitter and the second light-emitter to administer a dosage of UV light toward the card causing at least a partial sanitization of a surface of the card.

9. The card distribution and sanitization apparatus of claim 8, wherein at least one of the first light-emitter or the second light emitter is an elongated light-emitter.

10. The card distribution and sanitization apparatus of claim 9, wherein the elongated light-emitter is a light-emitting strip, the light-emitting strip comprising a number of light-emitting diode elements.

11. The card distribution and sanitization apparatus of claim 9, wherein the elongated light-emitter is an ultraviolet light-emitting tube.

12. The card distribution and sanitization apparatus of claim 8, further comprising a third light-emitter coupled to an internal wall of the housing, the third light-emitter configured to emit UV light onto the set of cards within the internal cavity.

13. The card distribution and sanitization apparatus of claim 12, further comprising a friction strip coupled to the internal wall of the housing, the friction strip configured to separate successive cards of the set of cards.

14. The card distribution and sanitization apparatus of claim 12, wherein:
the housing further comprises a lid; and
the controller causes the first light-emitter and the second light-emitter to stop emitting light when the lid is opened.

15. The card distribution and sanitization apparatus of claim 8, wherein the controller is configured to administer the dosage of UV light of at least 40 mJ/cm$^2$.

16. The card distribution and sanitization apparatus of claim 8, further comprising a proximity sensor, wherein the controller is configured to operate the first light-emitter and the second light-emitter to administer the dosage of UV light toward the card in response to the proximity sensor detecting the card.

17. A card distribution and sanitization apparatus comprising:
a housing defining:
an interior cavity configured to support a set of cards; and
a gap for a card of the set of cards to pass through, the gap positioned at a front portion of the housing; and
a light-emitting stack-up positioned proximate to the gap and configured to receive the card after the card passes through the gap, the light-emitting stack-up defining an inlet and a passage, the light-emitting stack-up comprising a pair of light-emitters positioned on opposing sides of the passage and configured to emit ultraviolet light toward the card.

18. The card distribution and sanitization apparatus of claim 17, wherein the pair of light-emitters are configured to emit ultraviolet-C light toward a respective card of the set of cards as the respective card passes through the passage.

19. The card distribution and sanitization apparatus of claim 18, wherein the pair of light-emitters are configured to administer a dosage of ultraviolet light of at least 40 mJ/cm$^2$.

20. The card distribution and sanitization apparatus of claim 17, further comprising:
an optical detector configured to measure a dosage value of ultraviolet light emitted from the pair of light-emitters; and
a controller configured to:
determine whether the dosage value meets or surpasses a threshold value; and
direct the pair of light-emitters to stop emitting ultraviolet light when the dosage value meets or surpasses the threshold value.

* * * * *